United States Patent [19]

Guy et al.

[11] Patent Number: 4,677,105
[45] Date of Patent: Jun. 30, 1987

[54] 2-ALKOXYCARBONYLALKYL-3-OXO-5,6-DIARYL-AS-TRIAZINES HAVING UTILITY AS THERAPEUTICS

[75] Inventors: Pitet Guy, Toulouse; Henri Cousse; Gilbert Mouzin, both of Castres, all of France

[73] Assignee: PF Medicament, Paris, France

[21] Appl. No.: 823,342

[22] Filed: Jan. 28, 1986

[30] Foreign Application Priority Data

Feb. 4, 1985 [FR] France ................ 85 01613

[51] Int. Cl.$^4$ ............... C07D 253/06; A61K 31/53
[52] U.S. Cl. ................................ 514/242; 544/182
[58] Field of Search ..................... 544/182; 514/242

[56] References Cited

U.S. PATENT DOCUMENTS

| | | | |
|---|---|---|---|
| 4,167,566 | 9/1979 | Pitet et al. | 544/182 |
| 4,188,387 | 2/1980 | Pitet et al. | 544/182 |

FOREIGN PATENT DOCUMENTS

| | | | |
|---|---|---|---|
| 36357 | 9/1981 | European Pat. Off. | 544/182 |
| 2368278 | 5/1978 | France. | |
| 2500830 | 9/1982 | France. | |
| 2478095 | 2/1983 | France. | |

*Primary Examiner*—John M. Ford
*Attorney, Agent, or Firm*—Gordon W. Hueschen

[57] ABSTRACT

2-Alkoxycarbonylalkyl-3-oxo-5,6-diaryl-as-Triazines of the formula I

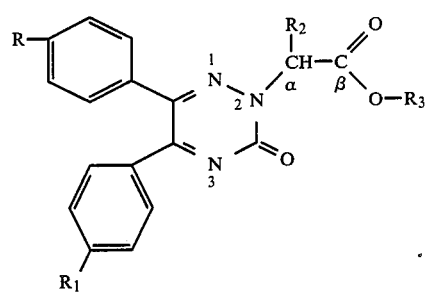

wherein
R and $R_1$, which may be identical or different, represent hydrogen, alkyl, alkoxy, hydroxy, dialkylamino, or halogen,
$R_2$ represents hydrogen or alkyl, and
$R_3$ represents alkyl, the method of preparation thereof, pharmaceutical compositions thereof, and a method of treating therewith, are all disclosed.

The compounds are useful as essentially non-antiinflammatory analgesics.

4 Claims, No Drawings

2-ALKOXYCARBONYLALKYL-3-OXO-5,6-DIARYL-AS-TRIAZINES HAVING UTILITY AS THERAPEUTICS

The present invention, made at the P. F. MEDICAMENT Research Center, has as its object new 2-alkoxycarbonylalkyl-3-oxo-5,6-diaryl-as-triazine derivatives, a method of synthesizing them, and their use in therapy. The new chemical compounds have general formula I:

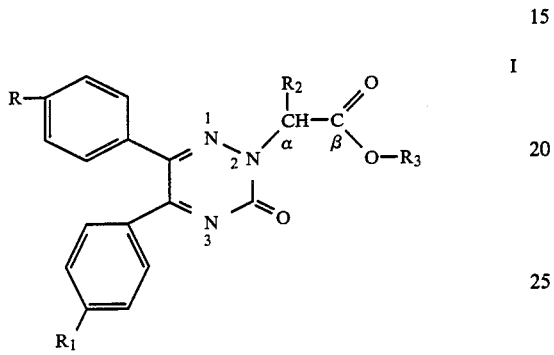

wherein
R and $R_1$, which may be identical or different, represent hydrogen, alkyl, alkoxy, hydroxy, dialkylamino, or halogen,
$R_2$ represents hydrogen or alkyl, and
$R_3$ represents alkyl.

Earlier work carried out on triazine derivatives having different functional groups on the nitrogen atom in the 2-position is illustrated by French Pat. Nos. 77 07245, 80 05959, and 81 04260, originating from the same Research Center. More recently, French Pat. No. 83 06107 concerning 2-N-cycloalkylmethyl-3-oxo-5,6-as-triazines emphasized the importances of certain specific substituents. Continuation of the investigations of this as-triazine structure has led to new derivatives which form the object of the present invention, being of formula I in which the functional group in 2-position is alkoxycarbonylalkyl.

Very surprisingly, these derivatives have little or no anti-inflammatory activity.

On the other hand, their analgesic activity is very pronounced. Representative compounds exhibited the following effects in the phenyl benzoquinone contortion test:

Example 3: $ED_{50} = 13$ mg/kg (Aspirin = 100 mg/kg (Glaphenine = 35 mg/kg)

Examples 4, 5, and 6: $ED_{50}$ respectively 11, 16, and 12 mg/kg.

The following Examples are given by way of illustration only but are not to be construed as limiting.

Synthesis Scheme

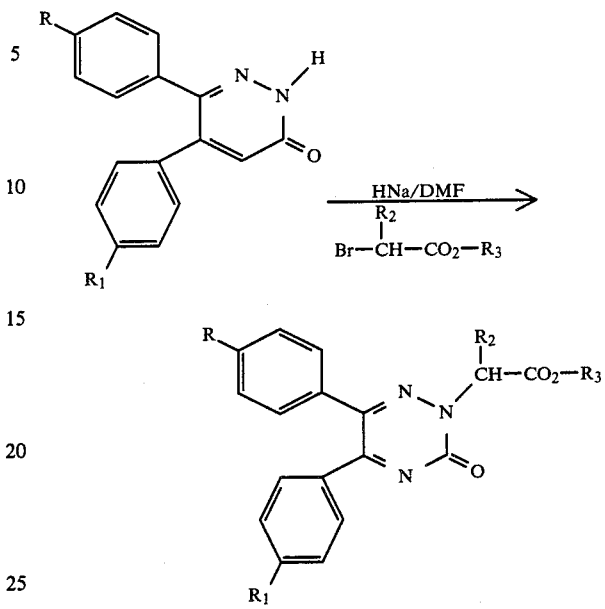

The triazine intermediates which are not substituted in 2-position have been prepared previously by the applicants from alpha-diketones and are disclosed in the above-cited prior art.

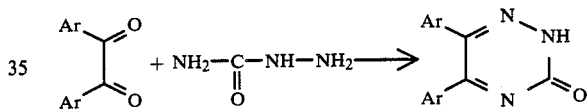

Ar = substituted or unsubstituted aryl groups.

Procedure:

One mole of triazine dissolved in dimethylformamide is treated with one mole of sodium hydride and then with the stoichiometric amount of an alkoxycarbonylalkyl bromide of the following formula, whereafter the reaction product is worked up and the product isolated in conventional manner.

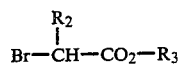

wherein another replaceable halogen atom may be present instead of the bromine atom.

EXAMPLE 1.

2-ethoxy carbonyl-methyl-3-oxo-5,6-di(paramethoxyphenyl)-as-triazine

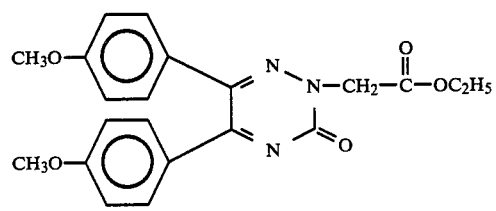

Yellow crystals.
Soluble in methylene chloride, chloroform, ether; alcohols and hot benzene.
Insoluble in water, dilute bases and acids.
Melting point: 153°±1° C.
TLC: benzene-ethyl acetate (7/3)—Rf: 0.23.
IR: νC=O : 1745 cm$^{-1}$.

EXAMPLE 2

2-(1-ethoxycarbonyl-1-ethyl)-3-oxo-5,6-di(parahydroxyphenyl)-as-triazine

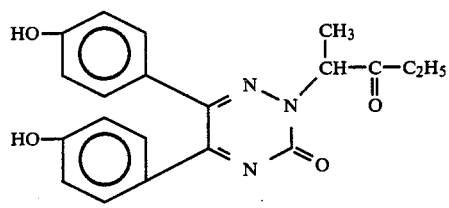

Yellow crystals.
Soluble in hot alcohols.
Insoluble in water, dilute bases and acids, benzene, chloroform, methylene chloride, ether.
Melting point: 276° C. TLC: chloroform-acetone (7:3)—Rf: 0.37
IR: νCO=1745 cm$^{-1}$

EXAMPLE 3

2-(1-ethoxycarbonyl-1-ethyl)-3-oxo-5,6-di(paramethoxyphenyl)-as-triazine

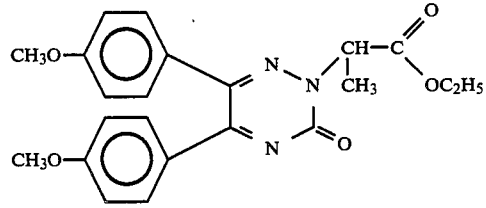

Yellow crystals.
Soluble in hot alcohols, benzene, chloroform, methylene chloride and ether.
Insoluble in water, dilute bases and acids.
Melting point: 132° C.
TLC: isopropyl ether, dioxane, triethylamine (85:12.5:2.5).

EXAMPLE 4

2-(1-ethoxycarbonyl-1-propyl)-3-oxo-5,6-di(paramethoxyphenyl)-as-triazine

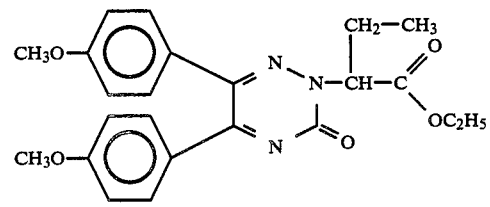

Yellow crystals.
Soluble in hot alcohols, benzene, methylene chloride, chloroform.
Insoluble in water, dilute bases and acids, ether.

Melting point: 110° C.

EXAMPLE 5

2-(1-ethoxycarbonyl-1-butyl)-3-oxo-5,6-di(paramethoxyphenyl)-as-triazine

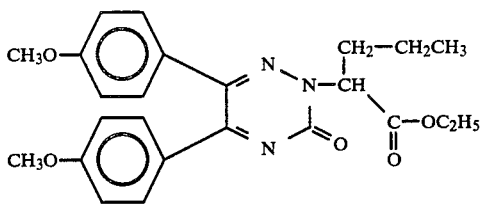

Yellow crystals.
Soluble in hot alcohols, benzene, methylene chloride, chloroform, ether.
Insoluble in water, dilute bases and acids.
Melting point: 110° C.

EXAMPLE 6

2-(1-methoxycarbonyl ethyl)-3-oxo-5,6-di(paramethoxyphenyl)-as-triazine

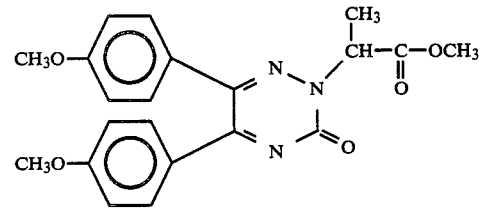

Yellow crystals.
Soluble in hot alcohols.
Insoluble: Water, ether.
Melting point: 137° C.

EXAMPLE 7

2-(1-ethoxycarbonyl-1-ethyl)-3-oxo-5,6-di(phenyl)-as-triazine

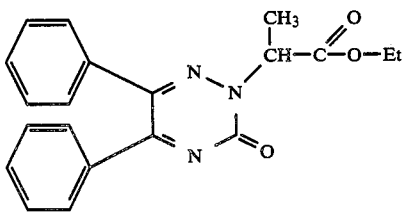

This compound is prepared in the same manner as given just preceding Example 1 and found to be an effective analgesic agent.

EXAMPLE 8

2-(1-ethoxycarbonyl-1-ethyl)-3-oxo-5,6-di(p-methyl-phenyl)-as-triazine

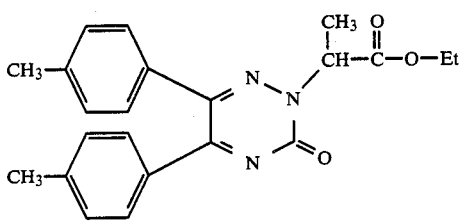

This compound is prepared in the same manner as given just preceding Example 1 and found to be an effective analgesic agent.

EXAMPLE 9

2-(1-ethoxycarbonyl-1-ethyl)-3-oxo-5,6-di(p-chlorophenyl)-as-triazine

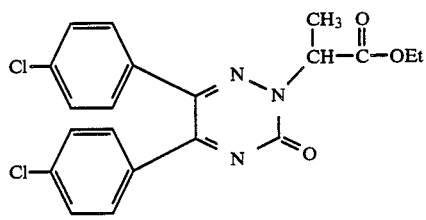

This compound is prepared in the same manner as given just preceding Example 1 and found to be an effective analgesic agent.

EXAMPLE 10

2-(1-ethoxycarbonyl-1-ethyl)-3-oxo-5,6-(p-chloro-p-methoxy)-5,6-as-triazine

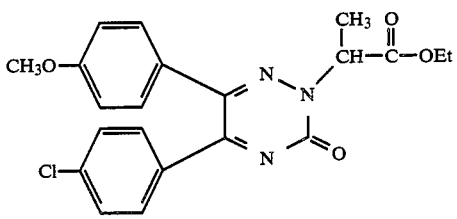

This compound is prepared in the same manner as given just preceding Example 1 and found to be an effective analgesic agent.

PHARMACOLOGICAL EXPERIMENTS

The pharmacological experiments were carried out at the pharmacological laboratory of the P. F. MEDICAMENT Research Center.

(A) Toxicology

The toxicological study was carried out on the customary mouse weighing about 20 g.

The substances were administered orally and the $LD_{50}$ expressed in mg/kg and calculated by the method of MILLER and TAINTER—Proc. Soc. Exper. Biol. Med. 1944, 57, 261.

Results: All the products tested and described in the above Examples have an $LD_{50}$ of more than 1000 mg/kg.

(B) Analgesic Properties

The activity in the phenyl benzoquinone contortion test of SIEGMUND et al., J. Pharm. Exptl. Ther. 1957, 119, 453, was determined by oral administration of the product.

Dose expressed in mg/kg in the mouse, 30 minutes before intraperitoneal injection of the algogenic agent.

The results are expressed in percentage variation of the number of contortions.

For the most active molecules we determined the $ED_{50}$.

| COMPOUND | ACTIVITY $ED_{50}$ mg/kg |
|---|---|
| Example 3 | 13 |
| Example 4 | 11 |
| Example 5 | 16 |
| Example 6 | 12 |
| Example 7 | 18 |
| Example 8 | 12 |
| Example 9 | 10 |
| Example 10 | 12 |
| Aspirin | 100 |
| Glaphenine | 35 |

THERAPEUTIC APPLICATIONS

In view of their excellent tolerance and their pharmacological properties, the products and most especially those described in Examples 3, 4, and 5, can be used in the treatment of algias or pains of various origins, e.g., tooth, muscular, or rheumatismal.

The active principles and pharmaceutical preparations containing the active principles can be administered orally, parenterally, or rectally. Such pharmaceutical compositions may also contain, associated therewith, other pharmaceutically- and therapeutically-acceptable active principles.

The unit dose will, for instance, be between about 10 and about 100 mg.

PHARMACEUTICAL COMPOSITIONS

The compounds of the invention, together with a conventional adjuvant, carrier, or diluent, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use; in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective analgesic amount of the active ingredient commensurate with the intended daily dosage range to be employed. Tablets containing ten (10) milligrams of active ingredient or, more broadly, ten (10) to one hundred (100) milligrams, per tablet, are accordingly suitable representative unit dosage forms.

METHOD OF TREATING

Due to their high degree of analgesic activity with essential absence of anti-inflammatory activity and their low toxicity, together presenting a most favorable therapeutic index, the compounds of the invention may be administered to a subject, e.g., a living animal body, in need to analgesic for the alleviation, treatment, or amelioration of a painful indication, preferably concurrently, simultaneously, or together with a pharmaceutically-acceptable carrier or diluent, especially and preferably in the form of a pharmaceutical composition thereof, whether by oral, rectal, or parenteral (including subcutaneous) route, in an effective analgesic amount. Suitable dosage ranges are 10–500 milligrams daily, preferably 50–250 milligrams daily, and especially 100–200 milligrams daily, depending as usual upon the exact mode of administration, form in which administered, the indication toward which the administration is directed, the subject involved and the body weight of the subject involved, and the preference and experience of the physician or veterinarian in charge.

In conclusion, from the foregoing, it is apparent that the present invention provides novel analgesic and essentially non-anti-inflammatory compounds, having advantageous and unpredictable properties, as well as novel pharmaceutical compositions thereof and method of treating therewith, all possessed of the foregoing more specifically-enumerated characteristics and advantages.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope of the appended claims.

We claim:

1. A 2-Alkoxycarbonylalkyl-3-oxo-5,6-diaryl-as-Triazine of the formula I

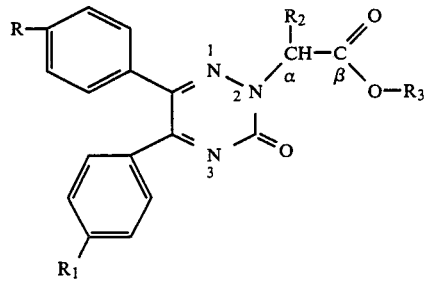

wherein
R and $R_1$, which may be identical or different, represent hydrogen, alkyl, alkoxy, hydroxy, dialkylamino, or halogen, any alkyl therein being $C_1$–$C_3$ alkyl,
$R_2$ represents hydrogen or $C_1$–$C_3$ alkyl, and
$R_3$ represents $C_1$ or $C_2$ alkyl.

2. A compound of claim 1, which is selected from the group consisting of:
2-ethoxycarbonyl-methyl-3-oxo-5,6-di(paramethoxyphenyl)-as-triazine
2-(1-ethoxycarbonyl-1-ethyl)-3-oxo-5,6-di(parahydroxyphenyl)-as-triazine
2-(1-ethoxycarbonyl-1-ethyl)-3-oxo-5,6-di(paramethoxyphenyl)-as-triazine
2-(1-ethoxycarbonyl-1-propyl)-3-oxo-5,6-di(paramethoxyphenyl)-as-triazine
2-(1-ethoxycarbonyl-1-butyl)-3-oxo-5,6-di(paramethoxyphenyl)-as-triazine
2-(1-methoxycarbonyl ethyl)-3-oxo-5,6-di(paramethoxyphenyl)-as-triazine
2-(1-ethoxycarbonyl-1-ethyl)-3-oxo-5,6-di(phenyl)-as-triazine
2-(1-ethoxycarbonyl-1-ethyl)-3-oxo-5,6-di(p-methylphenyl)-as-triazine
2-(1-ethoxycarbonyl-1-ethyl)-3-oxo-5,6-di(p-chlorophenyl)-as-triazine
2-(1-ethoxycarbonyl-1-ethyl)-3-oxo-5,6-(p-chlorophenyl)(p-methoxyphenyl)-as-triazine.

3. A pharmaceutical composition suitable for analgesic therapy containing an effective analgesic amount of a compound of claim 1 together with a pharmaceutically-acceptable diluent or carrier.

4. A method of treating a subject afflicted with pain comprising the step of administering to said subject an effective analgesic amount of a compound of claim 1.

* * * * *

UNITED STATES PATENT AND TRADEMARK OFFICE
CERTIFICATE OF CORRECTION

PATENT NO. : 4,677,105

DATED : June 30, 1987

INVENTOR(S) : Guy Pitet, Henri Cousse and Gilbert Mouzin

It is certified that error appears in the above-identified patent and that said Letters Patent is hereby corrected as shown below:

Title Page, under "United States Patent [19]; change "Guy et al." to read -- Pitet et al. --

Title Page, [75] Inventors:; "Pitet Guy" should read -- Guy Pitet --

Col. 7, line 2; "to" should read -- of --

Signed and Sealed this

Third Day of May, 1988

Attest:

DONALD J. QUIGG

Attesting Officer

Commissioner of Patents and Trademarks